United States Patent
Takeda et al.

(10) Patent No.: US 9,493,817 B2
(45) Date of Patent: *Nov. 15, 2016

(54) DECOMPOSITION METHOD AND DECOMPOSITION APPARATUS FOR NUCLEIC ACID POLYMER

(75) Inventors: Yoshihiro Takeda, Urayasu (JP);
Fumitaka Mafune, Tokyo (JP);
Tamotsu Kondou, Tokyo (JP)

(73) Assignee: Genesis Research Institute, Inc., Nagoya-shi, Aichi-ken (JP)

( * ) Notice: Subject to any disclaimer, the term of this patent is extended or adjusted under 35 U.S.C. 154(b) by 1551 days.

This patent is subject to a terminal disclaimer.

(21) Appl. No.: 11/713,749

(22) Filed: Mar. 5, 2007

(65) Prior Publication Data

US 2008/0217159 A1    Sep. 11, 2008

(51) Int. Cl.
*C12Q 1/68* (2006.01)
*G01N 33/543* (2006.01)

(52) U.S. Cl.
CPC ............... *C12Q 1/6813* (2013.01); *C12Q 1/68* (2013.01); *G01N 33/54346* (2013.01); *Y10S 977/773* (2013.01)

(58) Field of Classification Search
CPC ............................ C12Q 1/68; C12Q 1/6813
USPC ............... 435/243; 204/105, 157.61, 157.62; 536/23.1; 424/9.3, 9.34; 422/186.04; 977/911
See application file for complete search history.

(56) References Cited

U.S. PATENT DOCUMENTS

| 4,880,512 | A | 11/1989 | Cornelius et al. |
|---|---|---|---|
| 5,380,411 | A | 1/1995 | Schlief |
| 6,050,990 | A | 4/2000 | Tankovich et al. |
| 6,165,440 | A | 12/2000 | Esenaliev |
| 6,167,313 | A | 12/2000 | Gray et al. |
| 6,258,378 | B1 | 7/2001 | Schneider et al. |
| 6,530,944 | B2 | 3/2003 | West et al. |
| 6,685,927 | B2 | 2/2004 | Sumian et al. |

(Continued)

FOREIGN PATENT DOCUMENTS

| CA | 2 330 790 | 11/1999 |
|---|---|---|
| JP | 60-188161 | 9/1985 |

(Continued)

OTHER PUBLICATIONS

Zharov et al. "Self-assembling nanoclusters in living systems: application for integrated photothermal nanodiagnostics and nanotherapy" Nanomedicine: Nanotechnology, Biology, and Medicine 1 (2005) 326-345.*

(Continued)

*Primary Examiner* — Sharmila G. Landau
*Assistant Examiner* — Sean C Barron
(74) *Attorney, Agent, or Firm* — Finnegan, Henderson, Farabow, Garrett & Dunner, LLP

(57) ABSTRACT

A method for decomposing a target nucleic acid polymer, comprising: bonding a probe nucleic acid polymer and a microparticle to form a probe nucleic acid polymer-bonded microparticle, adding a target nucleic acid polymer to the probe nucleic acid polymer contained within the probe nucleic acid polymer-bonded microparticle to form an addition microparticle, and energizing the microparticle contained within the addition microparticle into a high-energy state and then using energy transfer from this high-energy state microparticle to decompose the target nucleic acid polymer.

8 Claims, 8 Drawing Sheets

(56) References Cited

U.S. PATENT DOCUMENTS

| | | |
|---|---|---|
| 6,955,639 B2 | 10/2005 | Hainfeld et al. |
| 6,989,007 B2 | 1/2006 | Shadduck |
| 7,263,445 B2 | 8/2007 | Fritzsche et al. |
| 2002/0103517 A1 | 8/2002 | West et al. |
| 2002/0197645 A1 | 12/2002 | Martin |
| 2003/0082633 A1 | 5/2003 | Martin et al. |
| 2003/0219892 A1 | 11/2003 | Palsson et al. |
| 2007/0187226 A1 | 8/2007 | Fuji |
| 2007/0292353 A1 | 12/2007 | Levy et al. |
| 2008/0160090 A1 | 7/2008 | Oraevsky et al. |
| 2009/0229968 A1 | 9/2009 | Takeda et al. |
| 2012/0046593 A1 | 2/2012 | Oraevsky et al. |

FOREIGN PATENT DOCUMENTS

| | | |
|---|---|---|
| JP | 4-152296 | 5/1992 |
| JP | 5-317047 | 12/1993 |
| JP | 6-81151 | 3/1994 |
| JP | 6-502549 | 3/1994 |
| JP | 9-75670 | 3/1997 |
| JP | 9-122479 | 5/1997 |
| JP | 10-508181 | 8/1998 |
| JP | 10-508581 | 8/1998 |
| JP | 2001-136970 | 5/2001 |
| JP | 2002-513590 | 5/2002 |
| JP | 2003-522149 | 7/2003 |
| JP | 2003-286509 | 10/2003 |
| JP | 2004-49105 | 2/2004 |
| JP | 2004-67657 | 3/2004 |
| JP | 2004-74018 | 3/2004 |
| JP | 2004-97910 | 4/2004 |
| JP | 2004-201701 | 7/2004 |
| JP | 2004-223345 | 8/2004 |
| JP | 2004-524134 | 8/2004 |
| JP | 2004-358583 | 12/2004 |
| JP | 2006-501050 | 1/2006 |
| WO | WO 93/03150 | 2/1993 |
| WO | WO 95/24489 | 9/1995 |
| WO | WO 96/09315 | 3/1996 |
| WO | WO 2004-023144 | 3/2004 |

OTHER PUBLICATIONS

Wailers et al. "DMA Degradation in Chinese Hamster Ovary Cells after Exposure to Hyperthermia" Cancer Research 42, 4427-4432, Nov. 1982.*

Neubauer et al. "DNA Degradation at Elevated Temperatures After Plasmid Amplification in Amino Acid—Starved *Escherichia coli* Cells" Biotechnology Letters vol. 18 No. 3 (Mar. 1996) pp. 321-326.*

Hu et al. "Heat Dissipation for Au Particles in Aqueous Solution: Relaxation Time versus Size" J. Phys. Chem. B 2002, 106, 7029-7033.*

Evens et al. "Evaluation of Degradation Pathways for Plasmid DNA in Pharmaceutical Formulations via Accelerated Stability Studies" Journal of Pharmaceutical Sciences, vol. 89, No. 1, Jan. 2000 pp. 76-87.*

Alivisatos et al. "Organization of 'nanocrystal molecules' using DNA" Nature, vol. 382, Aug. 15, 1996 pp. 609-611.*

Degradation—definition of degradation by the Free Online Dictionary, Thesaurus and Encyclopedia, http://www.thefreedictionary.com/p/degradation 3 pages, Accessed Jan. 18, 2011.*

Takahashi H et al. (2005). Controlled release of plasmid DNA from gold nanorods induced by pulsed near-infrared light. Chem Comm, issue 17, p. 2247-2249.*

Gerwitz DA (2000). Growth arrest and cell death in the breast cancer tumor cell in response to ionizing radiation and chemotherapeutic agents which induce DNA damage. Breast Cancer Research and Treatment, v62, p. 223-235.*

Borodulin. Site-specific cleavage of DNA with copper nitrofuran complex under X-ray and laser irradiation. Molekulyarnaya Biologiya (Moscow) (1996), v30(4), p. 801-807; original article in Russian with appended indexed English Abstract.*

Kim et al. Gold-nanoparticle-based miniaturized laser-induced fluorescence probe for specific DNA hybridization detection: studies on size-dependent optical properties. Nanotechnology (2006), v17, p. 3085-3093.*

Han et al. Light-Regulated Release of DNA and Its Deliveryto Nuclei by Means of Photolabile Gold Nanoparticles. Angew. Chem. (2006), v118, p. 3237-3241.*

Letfullin et al. Laser-induced explosion of gold nanoparticles: potential role for nanophotothermolysis. Nanomedicine (2006), v1(4), p. 473-480.*

Herdt et al. DNA dissociation and degradation at gold nanoparticle surfaces. Colloids and Surfaces B: Biointerfaces (2006), v51, p. 130-139.*

Notice of Grounds for Rejection for JP Appl. No. 2005-297943 dated Feb. 15, 2011.

Reply to Final Office Action filed Mar. 5, 2012 in U.S. Appl. No. 11/920,125 (11 pages).

Preliminary Remarks and Declaration Under 37 C.F.R. § 1.132 filed Mar. 7, 2012 in U.S. Appl. No. 11/920,125 (4 pages).

Radt et al., "Laser generated micro- and nanoeffects: inactivation of proteins coupled to gold nanoparticles with nano- and pico-second pulses," Laser-Tissue Interactions, Therapeutic Applications, and Photodynarnic Therapy. Proc. SPIE vol. 4433 (2001).

Huettman et al., "On the possibility of high precision photothermal microeffects and the measurement of fast thermal denaturation of proteins," IEEE J. of Selected Topics in Quantum Electronics, vol. 5, No. 4, Jul./Aug. 1999.

Office Action for U.S. Appl. No. 11/920,125 mailed Nov. 20, 2013.

Notice of Grounds for Rejection for Japanese Application No. 2005-136262 dated Oct. 11, 2011.

Notice of Grounds for Rejection for Japanese Application No. 2005-136262 dated Feb. 15, 2011.

Notice of Grounds for Rejection for Japanese Application No. 2005-136262 dated May 10, 2011.

Notice of Grounds for Rejection for Japanese Application No. 2005-136262 dated Jul. 26, 2011.

F. Mafune, et al., "Formation of Gold Nanoparticles by Laser Ablation in Aqueous Solution of Surfactant," J. Phys. Chem. B, 105 (2001), pp. 5114-5120.

Abstract of PCT WO 01/58458 A1 published Aug. 16, 2001.

Levy et al., "Nanochemistry: Synthesis and Characterization of Multifunctional Nanoclinics for Biological Applications," Chem. Mater. 2002, (14), pp. 3715-3721.

Kimura-Suda et al., "Base-Dependent Competitive Adsorption of Single-Stranded DNA on Gold," JACS Communications 125 (2003), pp. 9014-9015.

Demers et al., "Thermal Desorption Behavior and Binding Properties of DNA Bases and Nucleosides on Gold," JACS Communications 124 (2002), pp. 11248-11249.

N.H. Jang, "The Coordination Chemistry of DNA Nucleosides on Gold Nanoparticles as a Probe by SERS," Bull. Korean Chem. Soc. 2002, vol. 23, No. 12, pp. 1790-1800.

Peng et al., "Influence of Intense Pulsed Laser Irradiation on Optical and Morphological Properties of Gold Nanoparticle Aggregates Produced by Surface Acid-Base Reactions," Langmuir vol. 21, No. 10, pp. 4249-4253, May 10, 2005.

Gearheart et al., "Oligonucletide Adsorption to Gold Nanoparticles: a Surface-Enhanced Raman Spectroscopy Study of Intrinsically Bent DNA," J.Phys. Chem. B 2001, 105, pp. 12609-12615.

Hu et al., "Heat Dissipation for Au Particles in Aqueous Solution: Relaxation Time versus Size," J. Phys. Chem B 2002, 106, pp. 7029-7033.

Storhoff et al, "Sequence-Dependent Stability of DNA-Modified Gold Nanoparticles," Langmuir 2002, 18, pp. 6666-6670.

Petrovykh et al., "Quantitative Analysis and Characterization of DNA Immobilized on Gold," JACS (2003) 125, pp. 5219-5226.

Pitsilides et al., "Selective Cell Targeting with Light-Absorbing Microparticles and Nanoparticles," Biophysical Journal, v. 84 Jun. 2003, pp. 4023-4032.

(56) References Cited

OTHER PUBLICATIONS

O'Neal et al., "Photo-thermal tumor ablation in mice using near infrared-absorbing nanoparticles," Cancer Letters 209 (2004) pp. 171-176.

Loo et al., "Nanoshell-Enabled Photonics-Based Imaging and Therapy of Cancer," Tech. in Cancer Res. & Treatment., v. 3, No. 1, Feb. 2004, pp. 33-40.

Zharov et al., "Self-assembling nanoclusters in living systems; application for integrated photothermal nanodiagnostics and nanotherapy," Nanomedicine: Nanotechnology, Biology and Medicine 1 (2005) pp. 326-345.

Han et al., "Stability of Gold Nanoparticle-Bound DNA toward Biological, Physical, and Chemical Agents," Chem. Biol. Drug Des. 2006; 67: 78-82.

Li et al., "Assays Based on Differential Adsorption of Single-stranded and Double-stranded dNA on Unfunctionalized Gold Nanoparticles in a Colloidal Suspension," Plasmonics (2007) 4: 165-171.

Nelson, "The Adsorption of DNA onto Unmodified Gold Nanoparticles," Ph.D. thesis, Univ. Rochester 2008, Sec. 1.3, pp. 5-9.

Office Action dated Jan. 4, 2011 in U.S. Appl. No. 11/920,125, 11 pages.

Reply to Office Action filed Apr. 4, 2011 in U.S. Appl. No. 11/920,125, 9 pages.

Office Action dated Jun. 22, 2011 in U.S. Appl. No. 11/920,125, 10 pages.

Reply to Office Action filed Sep. 22, 2011 in U.S. Appl. No. 11/920,125, 7 pages.

Office Action dated Nov. 3, 2011 in U.S. Appl. No. 11/920,125, 13 pages.

Notice of Allowance and Notice of Allowability mailed Sep. 18, 2014 in U.S. Appl. No. 11/920,125.

* cited by examiner

SEQUENCE LISTING

```
<160> NUMBER OF SEQ ID NOS: 3

<210> SEQ ID NO 1
<211> LENGTH: 7249
<212> TYPE: DNA
<213> ORGANISM: Artificial Sequence
<220> FEATURE:
<223> OTHER INFORMATION: Description of Artificial Sequence: Synthetic
      M13mp18 vector

<400> SEQUENCE: 1
```

```
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttaca tggaatgaaa cttccagaca ccgtacttta     180
gttgcatatt taaaacatgt tgagctacag caccagattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tcttttgat gcaatccgct tgcttctga ctataatagt       420 cagggtaaag acctgatttt tgatttatgg tcattctcgt tttctgaact gtttaaagca     480
tttgaggggg attcaatgaa tatttatgac gattccgcag tattggacgc tatccagtct     540
aaacatttta ctattacccc ctctggcaaa acttcttttg caaaagcctc tcgctatttt     600 ggttttatc gtcgtctggt aaacgagggt tatgatagtg ttgctcttac tatgcctcgt      660
aattcctttt ggcgttatgt atctgcatta gttgaatgtg gtattcctaa atctcaactg     720
atgaatcttt ctacctgtaa taatgttgtt ccgttagttc gttttattaa cgtagatttt     780
tcttcccaac gtcctgactg gtataatgag ccagttctta aaatcgcata aggtaattca     840
caatgattaa agttgaaatt aaaccatctc aagcccaatt tactactcgt tctggtgttc     900
tcgtcagggc aagccttatt cactgaatga gcagctttgt tacgttgatt tgggtaatga     960
atatccggtt cttgtcaaga ttactcttga tgaaggtcag ccagcctatg cgcctggtct    1020
gtacaccgtt catctgtcct ctttcaaagt tggtcagttc ggttcccta tgattgaccg     1080 tctgcgcctc gttccggcta agtaacatgg agcaggtcgc ggatttcgac acaatttatc    1140
aggcgatgat acaaatctcc gttgtacttt gtttcgcgct tggtataatc gctggggtc     1200 aaagatgagt gttttagtgt attctttcgc ctctttcgtt ttaggttggt gccttcgtag    1260
tggcattacg tattttaccc gtttaatgga aacttcctca tgaaaaagtc tttagtcctc    1320
aaagcctctg tagccgttgc taccctcgtt ccgatgctgt ctttcgctgc tgagggtgac    1380
gatcccgcaa aagcggcctt taactccctg caagcctcag cgaccgaata tatcggttat    1440
gcgtgggcga tggttgttgt cattgtcggc gcaactatcg gtatcaagct gtttaagaaa    1500
ttcacctcga aagcaagctg ataaaccgat acaattaaag gctccttttg gagccttttt    1560
ttttggagat tttcaacgtg aaaaaattat tattcgcaat ccctttagtt gttccttttct   1620 attctcactc cgctgaaact gttgaaagtt gtttagcaaa accccataca gaaaattcat    1680
ttactaacgt ctggaaagac gacaaaactt tagatcgtta cgctaactat gagggttgtc    1740
tgtggaatgc tacaggcgtt gtagtttgta ctggtgacga aactcagtgt tacggtacat    1800
gggttcctat tgggcttgct atccctgaaa atgagggtgg tggctctgag ggtggcggtt    1860
ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcagggg cattaactgt ttatacgggc actgttactc      2100
aaggcactga ccccgttaaa acttattacc agtacactcc tgtatcatca aaagccatgt    2160
atgacgctta ctggaacggt aaattcagag actgcgcttt ccattctggc tttaatgaag    2220
atccattcgt ttgtgaatat caaggccaat cgtctgacct gcctcaacct cctgtcaatg    2280
ctggcggcgg ctctggtggt ggttctggtg cggctctga gggtggtggc tctgagggtg    2340
```

-continued

```
gcggttctga gggtggcggc tctgagggag gcggttccgg tggtggctct ggttccggtg      2400
attttgatta tgaaaagatg gcaaacgcta ataaggggc tatgaccgaa atgccgatg       2460 aaaacgcgct acagtctgac gctaaaggca aacttgattc tgtcgctact gattacggtg      2520
ctgctatcga tggtttcatt ggtgacgttt ccggccttgc taatggtaat ggtgctactg      2580
gtgattttgc tggctctaat tcccaaatgg ctcaagtcgg tgacggtgat aattcacctt      2640
taatgaataa tttccgtcaa tatttacctt ccctccctca atcggttgaa tgtcgccctt      2700
ttgtctttag cgctggtaaa ccatatgaat tttctattga ttgtgacaaa ataaacttat      2760
tccgtggtgt ctttgcgttt cttttatatg ttgccacctt tatgtatgta ttttctacgt      2820
ttgctaacat actgcgtaat aaggagtctt aatcatgcca gttcttttgg gtattccgtt      2880
attattgcgt ttcctcggtt tccttctggt aactttgttc ggctatctgc ttacttttct      2940 taaaagggc ttcggtaaga tagctattgc tatttcattg tttcttgctc ttattattgg      3000
gcttaactca attcttgtgg gttatctctc tgatattagc gctcaattac cctctgactt      3060
tgttcagggt gttcagttaa ttctcccgtc taatgcgctt ccctgttttt atgttattct      3120
ctctgtaaag gctgctattt tcattttga cgttaaacaa aaaatcgttt cttatttgga      3180 tgggataaa taatatggct gtttattttg taactggcaa attaggctct ggaaagacgc      3240
tcgttagcgt tggtaagatt caggataaaa ttgtagctgg gtgcaaaata gcaactaatc      3300
ttgatttaag gcttcaaaac ctcccgcaag tcgggaggtt cgctaaaacg cctcgcgttc      3360
ttagaatacc ggataagcct tctatatctg atttgcttgc tattgggcgc ggtaatgatt      3420
cctacgatga aaataaaaac ggcttgcttg ttctcgatga gtgcggtact ggtttaata      3480 cccgttcttg gaatgataag gaaagacagc cgattattga ttggtttcta catgctcgta      3540
aattaggatg gatattatt ttccttgttc aggacttatc tattgttgat aaacaggcgc      3600
gttctgcatt agctgaacat gttgtttatt gtcgtcgtct ggacagaatt actttacctt      3660
ttgtcggtac tttatattct cttattactg gctcgaaaat gcctctgcct aaattacatg      3720
ttggcgttgt taaatatggc gattctcaat taagccctac tgttgagcgt tggctttata      3780
ctggtaagaa tttgtataac gcatatgata ctaaacaggc ttttctagt aattatgatt      3840 ccggtgttta ttcttatta acgccttatt tatcacacgg tcggtatttc aaaccattaa      3900
atttaggtca gaagatgaaa ttaactaaaa tatatttgaa aaagttttct cgcgttcttt      3960
gtcttgcgat tggatttgca tcagcattta catatagtta tataacccaa cctaagccgg      4020
aggttaaaaa ggtagtctct cagacctatg attttgataa attcactatt gactcttctc      4080
agcgtcttaa tctaagctat cgctatgttt tcaaggattc taagggaaaa ttaattaata      4140
gcgacgattt acagaagcaa ggttattcac tcacatatat tgatttatgt actgtttcca      4200
ttaaaaaagg taattcaaat gaaattgtta atgtaatta attttgtttt cttgatgttt      4260
gtttcatcat cttcttttgc tcaggtaatt gaaatgaata attcgcctct gcgcgatttt      4320
gtaacttggt attcaaagca atcaggcgaa tccgttattg tttctcccga tgtaaaaggt      4380
actgttactg tatattcatc tgacgttaaa cctgaaaatc tacgcaattt ctttatttct      4440
gttttacgtg ctaataattt tgatatggtt ggttcaattc cttccataat tcagaagtat      4500
aatccaaaca atcaggatta tattgatgaa ttgccatcat ctgataatca ggaatatgat      4560
gataattccg ctccttctgg tggtttcttt gttccgcaaa atgataatgt tactcaaact      4620
tttaaaatta ataacgttcg ggcaaaggat ttaatacgag ttgtcgaatt gtttgtaaag      4680
tctaatactt ctaaatcctc aaatgtatta tctattgacg gctctaatct attagttgtt      4740
```

```
agtgcaccta aagatatttt agataacctt cctcaattcc tttctactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aatattgtc tgtgccacgt     5040 attcttacgc tttcaggtca aaggggttct atctctgttg ccagaatgt cccttttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caagattctg gcgtaccgtt cctgtctaaa    5400
atccctttaa tcggcctcct gtttagctcc cgctctgatt ccaacgagga agcacgtta    5460 tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccctt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac ggtcgtcgtc ccctcaaact    6540
ggcagatgca cggttacgat gcgcccatct acaccaacgt aacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa cgcgaatttt aacaaaatat taacgtttac    6780
aatttaaata tttgcttata caatcttcct gttttggggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct cacccttttg aatctttacc tacacattac tcaggcattg catttaaaat    7080
```

```
atatgagggt tctaaaaatt tttatccttg cgttgaaata aaggcttctc ccgcaaaagt    7140
attacagggt cataatgttt ttggtacaac cgatttagct ttatgctctg aggctttatt    7200
gcttaatttt gctaattctt tgccttgcct gtatgattta ttggatgtt               7249

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aattctgtcc agacgacgac aataaacaac atgttcagct aatgcagaac                50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacatccaat aaatcataca ggcaaggcaa agaattagca aaattaagca                50
```

DECOMPOSITION METHOD AND DECOMPOSITION APPARATUS FOR NUCLEIC ACID POLYMER

BACKGROUND

1. Technical Field

The present invention relates to a nucleic acid polymer decomposition method and decomposition apparatus for decomposing a specific site of a nucleic acid polymer.

2. Related Art

Examples of conventional methods of decomposing specific sites of nucleic acid polymers such as DNA and RNA include methods that involve the cleavage of specific sites within DNA using restriction enzymes. These restriction enzymes are mainly enzymes that catalyze the site-specific cleavage of double-stranded DNA, and all of the DNA cleavage operations proceed via hydrolysis of phosphate diester bonds. Furthermore, DNA ligase can be used to freely bond cleavage fragments with other DNA fragments.

Furthermore, methods of cleaving DNA at specific sites using chemically synthesized molecules are also conventional. For example, National Stage Laid-Open No. Hei 10-508581 based on PCT/US95/12312 discloses a method in which a texaphyrin is used as the chemically synthesized molecule, and this texaphyrin is covalently bonded to an oligonucleotide, thereby enabling site-specific cleavage of DNA. In this case, the DNA cleavage is a photolytic cleavage. The cleavage is thought to be neither a hydrolysis (in which a water molecule is added across the bond causing the bond to break), nor a simple oxidation (in which an oxidation reaction causes the bond breakage in the absence of light). At present, details relating to the mechanism of the cleavage remain unclear.

Furthermore, methods of cleaving DNA at specific sites using ribozymes are also conventional. For example, National Stage Laid-Open No. Hei 10-508181 based on PCT/US95/02816 discloses a method in which any RNA can be targeted for specific cleavage by RNase P derived from prokaryotic or eukaryotic cells using a suitably designed oligonucleotide, namely an external guide sequence, to form a hybrid with the target RNA. This method is useful in preventing expression of the function of the target RNA, and in preventing the expression of disease or disorder-causing genes in vivo. Furthermore, with this method, in the same manner as was described above for nucleic acid cleavage using restriction enzymes, all DNA cleavages proceed via hydrolysis of phosphate diester bonds, and DNA ligase can be used to freely bond cleavage fragments with other DNA fragments.

However, with DNA cleavage methods that use restriction enzymes, the cleavage site is a DNA sequence site determined in advance by the nature of the enzyme, and cleavage at any position is problematic. Furthermore, temporospatial control of nucleic acid cleavage by enzymes is also difficult. Moreover, in those cases where the base at the RNA cleavage site has been modified by methylation or the like, the efficiency of the cleavage deteriorates.

Furthermore, in the method of Japanese Publication of unexamined PCT Patent Application No. Hei 10-508581 based on PCT/US95/12312, temporospatial control of the enzyme-based nucleic acid cleavage is difficult.

In addition, in the method of National Stage Laid-Open No. Hei 10-508181 based on PCT/US95/02816, the cleavage by a ribozyme is also a cleavage by an enzyme, and consequently, in the same manner as that observed for nucleic acid cleavage by restriction enzymes, temporospatial control is difficult. Furthermore, in the same manner as that observed for nucleic acid cleavage by restriction enzymes, cleavage by a ribozyme also suffers from a deterioration in the cleavage efficiency if the base at the DNA or RNA cleavage site has been modified by methylation or the like.

SUMMARY

The present invention provides a method and apparatus for decomposing a nucleic acid polymer that enables decomposition of a specific site of the nucleic acid polymer with favorable temporospatial control.

The present invention provides a method for decomposing a target nucleic acid polymer, comprising: bonding a probe nucleic acid polymer and a microparticle to form a probe nucleic acid polymer-bonded microparticle, adding the target nucleic acid polymer to the probe nucleic acid polymer contained within the probe nucleic acid polymer-bonded microparticle to form an addition microparticle, and energizing the microparticle contained within the addition microparticle into a high-energy state and then using energy transfer from the high-energy state microparticle to decompose the target nucleic acid polymer.

In the present invention, by using the probe nucleic acid polymer bonded to the microparticle to form a specific complementary strand pair at a specific site within the target nucleic acid polymer (hereafter, this process is referred to using the terms "hybridize" and "hybridization"), and then elevating the microparticle into a high-energy state, temporospatial control can be achieved, enabling cleavage to be realized at a site on the target nucleic acid polymer in close proximity to the microparticle.

Furthermore, the present invention also provides an apparatus for decomposing a target nucleic acid polymer, comprising a housing unit that houses an addition microparticle generated by bonding a probe nucleic acid polymer and a microparticle and then adding a target nucleic acid polymer to the probe nucleic acid polymer, and an energy supply device that energizes the microparticle contained within the addition microparticle into a high-energy state, wherein energy transfer from the high-energy state microparticle is used to decompose the target nucleic acid polymer.

In the present invention, a nucleic acid polymer decomposition apparatus can be provided in which, by using the probe nucleic acid polymer bonded to the microparticle to form a specific complementary strand pair at a specific site within the target nucleic acid polymer, and then elevating the microparticle into a high-energy state, temporospatial control can be achieved, enabling cleavage to be realized at a site on the target nucleic acid polymer in close proximity to the microparticle.

DETAILED DESCRIPTION

Figure 1:
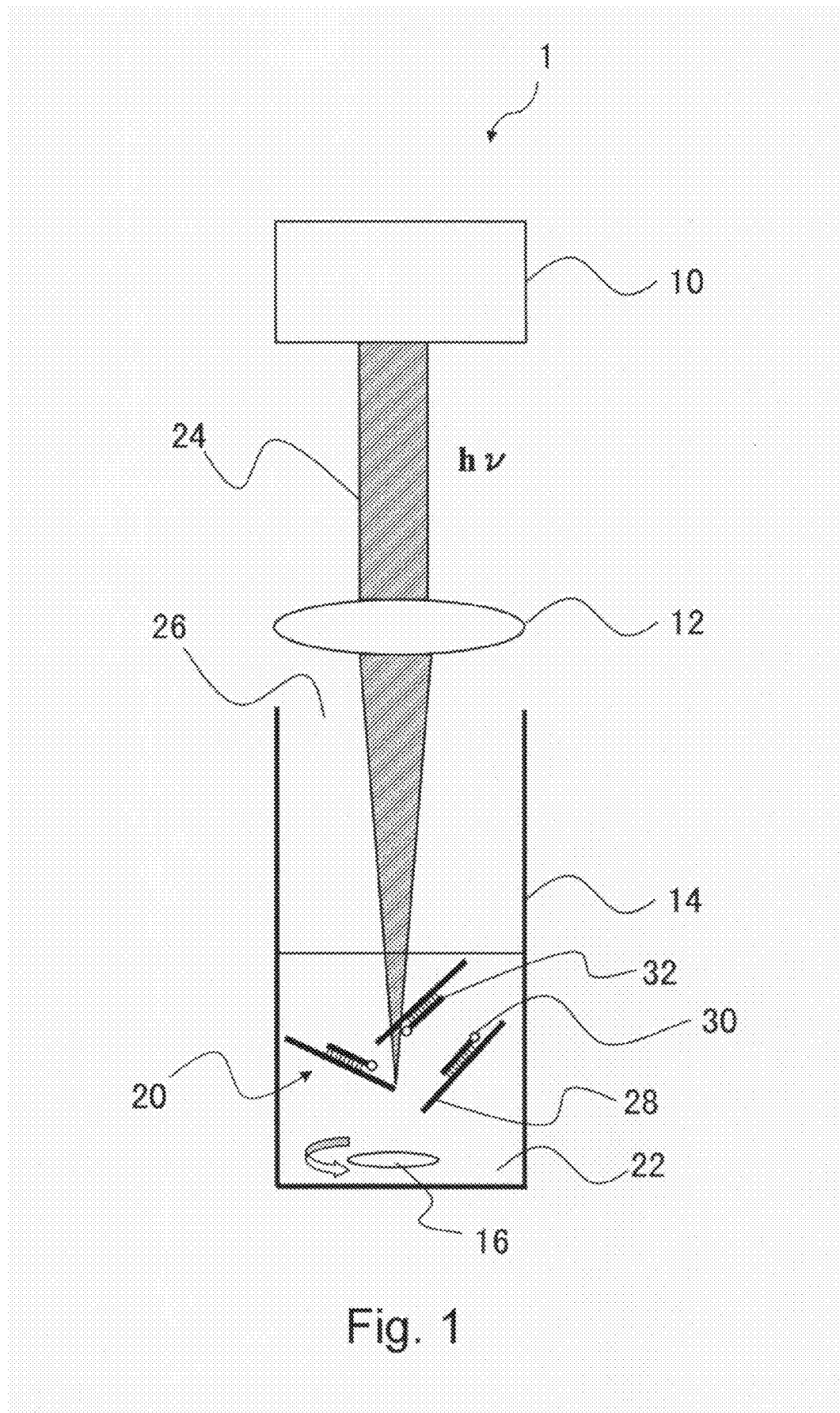
FIG. 1 is diagram showing an example of the structure of a nucleic acid polymer decomposition apparatus according to an embodiment of the present invention.

As follows is a description of embodiments of the present invention. In this description, the term "high-energy state" refers to any state that is at a higher energy level than the normal state, even if the energy difference between the higher energy level and the normal level is small. This includes rovibrational excitation of the atoms or molecules that constitute the microparticles, electron excitation, collective electron excitation, thermal energy generated by relaxation from an exited state, component particles, ions, electrons or radicals of microparticles having high energy, and plasma states. Furthermore, this high-energy state also includes cases in which the forms of energy described above undergo relaxation via the surrounding solvent, thereby placing the solvent itself in a high-energy state, as well as physical states that do not exist at normal temperature and normal pressure, and high-pressure states. Furthermore, the expression "near the surface" refers specifically to the region that extends preferably no more than approximately 100 nm, and even more preferably no more than approximately 10 nm, and most preferably no more than approximately 1 nm, externally or internally from the microparticle surface.

As follows is a description of a nucleic acid polymer decomposition method according to an embodiment of the present invention.

(1) Formation of a Probe Nucleic Acid Polymer-Bonded Microparticle by Bonding a Probe Nucleic Acid Polymer and a Microparticle First, a probe nucleic acid polymer that undergoes complementary addition at a specific site within a target nucleic acid polymer is bonded to a microparticle, thereby forming a probe nucleic acid polymer-bonded microparticle. The probe nucleic acid polymer is at least one of DNA, RNA and PNA. By designing the probe nucleic acid polymer so that it undergoes complementary addition to the cleavage target site within the target nucleic acid polymer, specificity can be imparted at that target site within the target nucleic acid polymer. In this case, there are none of the types of limitations associated with imparting specificity using restriction enzymes.

There are no particular restrictions on the length of the probe nucleic acid polymer, although the use of a polymer with a length within a range from approximately 10 mer to approximately 50 mer is preferred as it facilitates addition to the target nucleic acid polymer. In order to ensure favorable precision of the target nucleic acid polymer decomposition site, the probe nucleic acid polymer is preferably as long as possible. Furthermore, although there are no particular restrictions on the quantity of probe nucleic acid polymer molecules used in relation to the number of microparticles, quantities within a range from 1 to several dozen, namely from 1 to approximately 50 polymer molecules per microparticle, are preferred.

Examples of suitable methods of bonding the probe nucleic acid polymer and the microparticle include methods that involve altering factors such as the solution pH or the ionic state of the probe nucleic acid polymer. Examples include methods in which the probe nucleic acid polymer is selectively adsorbed onto the microparticle surface, methods in which the microparticle surface is modified so as to develop affinity for the probe nucleic acid polymer, and methods in which the probe nucleic acid polymer is modified so as to develop affinity for the microparticle surface, as well as methods that employ other techniques to effect chemical bonding (such as ionic bonding, covalent bonding, coordination bonding, metal bonding, hydrogen bonding, or van der Waals bonding) between the probe nucleic acid polymer and the microparticle surface, methods in which the probe nucleic acid polymer is buried near the surface of the microparticle surface, or methods in which a terminal of the probe nucleic acid polymer is chemically modified to facilitate bonding to the microparticle, that is, in an example where a gold microparticle is used as the microparticle and DNA is used as the probe nucleic acid polymer, a method in which a DNA terminal that has been modified by thiol labeling or the like is prepared, and this modified DNA is then bonded to the surface of the gold microparticle. In addition to the above thiol labeling, other examples of suitable chemical modifications of a terminal of the probe nucleic acid polymer include biotinylation labeling and digoxigenation.

In some cases, the use of PNA as the probe nucleic acid polymer can be particularly effective. PNA is an abbreviation of "Peptide Nucleic Acid", and is a chemically synthesized nucleic acid analogue that has been developed as an alternative to nucleic acids (DNA and RNA). PNA is a material in which the sugar-phosphate backbone that represents the basic backbone structure of a nucleic acid is substituted with a polyamide backbone comprising glycine units, and has a three dimensional structure very similar to that of a nucleic acid. PNA offers the advantages described below.

(a) PNA bonds far more specifically and more powerfully to a complementary nucleic acid than a probe DNA or probe RNA. Furthermore, PNA penetrates the double strands of a nucleic acid and hybridizes with complementary sites.

(b) The hybridization reaction between PNA and the target nucleic acid polymer occurs rapidly, meaning the reaction time can be shortened dramatically compared with the reaction times required for DNA or RNA probe nucleic acid polymers.

(c) PNA has an uncharged, neutral and stable backbone structure, and consequently undergoes hybridization without being affected by factors such as the solution pH or salt concentration.

(d) Because PNA is a chemically synthesized material that does not exist in vivo, it undergoes no substantial decomposition by nucleic acids, protein-decomposing enzymes, hydrolysis or the like.

Suitable examples of the microparticles used in the present embodiment of the present invention include metallic microparticles, non-metallic microparticles, and polymer microparticles. Furthermore, composite microparticles incorporating an organic dye or the like that absorbs laser radiation or the like are also suitable. In addition, the microparticle surface may also be modified to impart the microparticle with superior affinity with the probe nucleic acid polymer.

There are no particular restrictions on the types of metallic microparticles that can be used, and microparticles of typical metals or transition metals are suitable, including transition metals such as Ti, V, Cr, Mn, Fe, Co, Ni, Cu, Sc, Y, Zr, Nb, Mo, Tc, Hf, Ta, W, Au, Ag, Ru, Rh, Pd, Os, Ir, Pt, Re, lanthanoids, and actinoids, as well as other metals such as Zn, Cd, Hg, Al, Ga, In, Tl, Si, Ge, Sn, Pb, As, Sb, and Bi. Of the transition metals, Au, Ag, Ru, Rh, Pd, Os, Ir, Pt, Cu, Fe, Ni, Co, Cr, Mn, Mo, W, Ta and Nb are preferred, the noble metals such as Au, Ag and the platinum group metals (Ru, Rh, Pd, Os, Ir and Pt) are particularly preferred due to their resistance to oxidation, and Au and Pt are particularly desirable. Furthermore, metallic microparticles such as Au and Pt that exhibit strong light absorption via surface plasmon resonance, interband transitions or the like are particularly preferred. Moreover, metallic particles such as Au, Ag and Cu for which the surface plasmon resonance band occurs within the visible light region are particularly desirable. Composite metal microparticles such as GaAs, GaTe and CdSe are also suitable.

Examples of suitable non-metallic microparticles include microparticles of organic compounds such as organic dyes and organic pigments, and microparticles of inorganic compounds such as inorganic pigments.

Examples of suitable polymer microparticles include polystyrene, polyethylene, polypropylene and latex microparticles. Furthermore, organic compounds such as organic dyes or organic pigments, and inorganic compounds such as inorganic pigments may also be incorporated within the polymer microparticles, and groups that exhibit strong light absorption may be chemically bonded to the polymer microparticles.

In order to achieve a favorably high dispersibility of the microparticles within the solution, the average particle size of the microparticles is preferably no more than approximately 100 μm, is even more preferably within a range from approximately 1 nm to approximately 100 nm, and is most preferably within a range from approximately 1 nm to approximately 10 nm. If the average particle size of a metallic microparticle is less than approximately 1 nm, then the wavelength of the irradiating laser or the like tends to shift to a shorter wavelength, which can make the operation overly complex. Furthermore, because the scope of the target material decomposition reaction can be controlled by altering the average particle size of the microparticles, the average particle size of the microparticles may be selected in accordance with factors such as the purpose of the decomposition. The average particle size of the microparticles can be measured, for example, using a light scattering measurement apparatus (DLS-7000) manufactured by Otsuka Electronics Co., Ltd.

There are no particular restrictions on the method used for producing metallic microparticles, and suitable methods include SF-LAS methods (surfactant-free laser ablation in solution) in which the surface of a metal plate in a liquid such as water is ablated by laser irradiation or microwave irradiation, SC-LAS methods (surfactant-controlled laser ablation in solution) in which the surface of a metal plate in a liquid such as water containing an added surfactant is ablated by laser irradiation or microwave irradiation, chemical reduction methods, and methods that involve electrical discharge within solution. Adding a surfactant to the metallic microparticles enables the metallic microparticles to be better stabilized, which is preferred in terms of factors such as facilitating operations within the production process.

Examples of surfactants that can be used include anionic, cationic, nonionic and amphoteric surfactants. For reasons including the surfactant solubility and the stabilizing force imparted to the metallic microparticles within the solution, sodium dodecylsulfate (SDS) is usually used.

(2) Formation of Addition Microparticles by Adding the Target Nucleic Acid Polymer to the Probe Nucleic Acid Polymer Contained within the Probe Nucleic Acid Polymer-Bonded Microparticles Subsequently, the target nucleic acid polymer is added to the probe nucleic acid polymer contained within the aforementioned probe nucleic acid polymer-bonded microparticles. In other words, the probe nucleic acid polymer forms a specific complementary pair at a specific site within the target nucleic acid polymer, thus forming an addition microparticle. For example, in the case where microparticles obtained by bonding a probe DNA to gold microparticles are used as the aforementioned probe nucleic acid polymer-bonded microparticles, a solution containing the probe nucleic acid polymer-bonded microparticles, and a solution containing a target DNA as the target nucleic acid polymer are mixed together and hybridized.

The reaction temperature during hybridization is typically within a range from approximately 25° C. to approximately 75° C., and is preferably within a range from approximately 30° C. to approximately 40° C. Furthermore, the reaction time is typically within a range from approximately 1 hour to approximately 48 hours, and is preferably within a range from approximately 5 hours to approximately 12 hours. In those cases where the length of the probe DNA is considerable, raising the reaction temperature to reduce tangling of the DNA tends to facilitate the hybridization process. For example, hybridization can be conducted by mixing together a solution containing the probe nucleic acid polymer-bonded microparticles and a solution containing a target DNA as the target nucleic acid polymer, and then holding the mixed solution at a temperature of approximately 60° C. for a period of 24 hours.

Additives may also be added to ensure that a more efficient hybridization occurs. In solutions containing a surfactant (such as SDS, NP-40 (polyoxyethylene (9) octyl phenyl ether)) and an organic solvent (such as formamide or acetic acid), secondary structures of the target nucleic acid polymer such as DNA or RNA are destroyed, which offers the advantage of facilitating the approach of the probe nucleic acid polymer.

(3) Decomposing the Target Nucleic Acid Polymer by Energizing the Microparticles into a High-Energy State Finally, the microparticles contained within the addition microparticles are elevated to a high-energy state, and energy transfer from the high-energy state microparticles into the immediate surroundings is used to decompose the target nucleic acid polymer at a specific site.

A schematic illustration of an example of a nucleic acid polymer decomposition apparatus according to an embodiment of the present invention is shown in FIG. 1, and this apparatus is described below. The decomposition apparatus 1 comprises a laser generator 10 that functions as an energy supply device, a lens 12 that acts as a light focusing device, a cell 14 that functions as a housing unit, and a stirring bar 16 that functions as a dispersion device.

Describing the decomposition apparatus 1 in further detail, the stirring bar 16 is provided inside the base of the cell 14, which is a closed square-shaped cylinder for example, the lens 12 is positioned above an opening 26 of the cell 14 as shown in FIG. 1, and the laser generator 10 is provided above the lens 12 in FIG. 1.

As follows is a description of the operation of the nucleic acid polymer decomposition apparatus 1 according to the present embodiment, based on FIG. 1. First, a reaction liquid 22 containing addition microparticles 20 is prepared and placed inside the cell 14. Usually, the addition microparticles 20 are in a dispersed state within the reaction liquid 22.

Subsequently, with the reaction liquid 22 undergoing constant stirring using the stirring bar 16, a laser 24 emitted from the laser generator 10 is focused by the lens 12, and irradiated into the reaction liquid 22 inside the cell 14. If the laser 24 is irradiated into the reaction liquid 22 in which the addition microparticles 20 are dispersed at a predetermined intensity and for a predetermined period of time, then the microparticles 30 within the addition microparticles 20 are elevated to a high-energy state, and energy transfer from these high-energy state microparticles 30 into the immediate surroundings decomposes a target nucleic acid polymer 28 that exists near the surface of the microparticles 30 at a specific site within the target nucleic acid polymer 28. In order to improve factors such as the decomposition efficiency and the site selectivity, when the laser 24 is irradiated into the reaction liquid 22, the laser 24 is preferably focused at a point within the reaction liquid 22, using the lens 12 or the like that functions as the light focusing device.

The target nucleic acid polymer 28 that acts as the decomposition target in the present embodiment is at least one of a DNA and RNA. If the target nucleic acid polymer 28 is a nucleic acid, then either a single-stranded or double-stranded nucleic acid is suitable. In the case of a double-stranded nucleic acid, the use of a PNA as the probe nucleic acid polymer enables the probe to efficiently penetrate the double-stranded nucleic acid and hybridize with complementary sites.

There are no particular restrictions on the solvent used in the reaction liquid 22, provided the solvent is capable of uniformly dispersing, suspending or dissolving the addition microparticles 20, and suitable solvents include water and typical organic solvents. There are no particular restrictions on the water used, and tap water, artesian water, or purified or ultra-purified water such as ion-exchanged water are suitable, although from the viewpoint of improving the decomposition efficiency, minimal quantities of impurities are preferred, and purified or ultra-purified water such as ion-exchanged water is typically used. Examples of suitable organic solvents that can be used include alcohol-based solvents such as methanol, ethanol and isopropyl alcohol, aromatic solvents such as benzene and toluene, halogenated solvents such as methylene chloride, chloroform and carbon tetrachloride, straight-chain saturated hydrocarbon-based solvents such as n-hexane and n-heptane, cyclic saturated hydrocarbon-based solvents such as cyclohexane, and acetonitrile and the like. Of these, water or alcohol-based solvents are preferred as they can be used across a broader range of applications, and water is particularly desirable.

There are no particular restrictions on the concentration of the addition microparticles 20 within the reaction liquid 22, provided the concentration is at a level that enables favorable suspension or dispersion of the addition microparticles 20, although a typical concentration is usually no higher than approximately $10^{15}$ particles/mL.

Although there are no particular restrictions on the quantity of the target nucleic acid polymer 28 used in relation to the quantity of the microparticles 30, typically the quantity of target nucleic acid polymer molecules is within a range from 1 to several dozen, for example from 1 to approximately 50 polymer molecules, per single microparticle.

There are no particular restrictions on the cell 14 that functions as the housing unit for holding the reaction liquid 22 containing the addition microparticles 20, and typically a cell formed from a material such as quartz or glass is used. A substrate of glass, silicon, an organic polymer such as an acrylic polymer, or an inorganic material such as sapphire or alumina may also be used as the housing unit instead of the cell 14.

In the present embodiment, a laser was irradiated onto the addition microparticles 20 to elevate the microparticles 30 to a high-energy state, but any device capable of elevating the microparticles 30 to a high-energy state could be used, and for example, irradiation could also be conducted using electromagnetic radiation such as microwaves, visible light, ultraviolet light, infrared light, X-rays or γ-rays, or sound waves (elastic waves). Amongst the various forms of electromagnetic radiation, microwaves, visible light, ultraviolet light and infrared light are preferred, and lasers may also be used. Furthermore, ultrasound is preferred in the case of sound waves.

As described above, the term "high-energy state" refers to any state that is at a higher energy level than the normal state, even if the energy difference is small, and for example in the case of irradiation with pulsed laser light with a wavelength of approximately 532 nm, the microparticles 30 absorb a single photon of laser light, and adopt a high-energy state that is at least 5 eV higher than the normal state.

The energy density of the laser 24 irradiated into the reaction liquid 22 is of a density that is insufficient to generate a plasma within the water, and is typically within a range from approximately $0.1$ mW/cm$^2$ to approximately $10^{10}$ W/cm$^2$, and preferably within a range from approximately $0.1$ mW/cm$^2$ to approximately $10$ W/cm$^2$.

The focus region into which the light such as the laser 24 is focused is typically of a volume within a range from approximately $(1\ \mu m)^3$ to approximately $(1\ mm)^3$, and is preferably within a range from approximately $(1\ \mu m)^3$ to approximately $(0.2\ mm)^3$. Because of apparatus restrictions, shrinking the focus region to a volume smaller than approximately $(1\ \mu m)^3$ is problematic, whereas if the focus region is larger than approximately $(1\ mm)^3$, then the decomposition efficiency may decrease. Furthermore, the irradiation of the laser 24 or the like may use either pulsed or continuous irradiation.

There are no particular restrictions on the intensity of the laser 24 or the like irradiated into the reaction liquid 22, provided the intensity is sufficient to elevate the microparticles 30 to a high-energy state and effect efficient decomposition of the target nucleic acid polymer 28, although in the case of a pulsed laser, the intensity is preferably within a range from approximately 100 µJ/pulse to approximately 100 mJ/pulse, and is even more preferably within a range from approximately 1 mJ/pulse to approximately 20 mJ/pulse. In the case of a continuous wave laser (CW laser), an intensity within a range from approximately 0.1 mW to approximately 10 W is preferred. A large intensity for the laser 24 improves the decomposition efficiency of the target nucleic acid polymer 28, but if the irradiation intensity of the laser 24 is lower than approximately 100 µj/pulse, then the decomposition of the target nucleic acid polymer 28 may not proceed, whereas if the intensity is larger than approximately 100 mJ/pulse, then depending on the size of the focus region, the solvent itself may undergo dielectric breakdown or the container (the cell) may suffer damage. Because the scope of the decomposed portion of the target nucleic acid polymer 28 increases in size as the intensity of the laser 24 or the like is increased, the scope of the decomposition of the target nucleic acid polymer 28 can be controlled by adjusting the laser intensity.

Although there are no particular restrictions on the time period for which the reaction liquid 22 is irradiated with the laser 24 or the like, a typical period is within a range from approximately the time of a single pulse width to a time of approximately 100 minutes, and is preferably within a range from approximately the time of a single pulse width to approximately 10 minutes. In the case of a pulsed laser, there are no particular restrictions on the pulse frequency, but a frequency within a range from approximately 5 Hz to approximately 20 Hz is preferred.

There are no particular restrictions on the wavelength of the laser 24 or the like irradiated into the reaction liquid 22, and a wavelength that enables efficient elevation of the microparticles 30 to a high-energy state may be selected in accordance with the nature of the microparticles 30. For example, in those cases where metallic microparticles are used as the microparticles 30, a wavelength that is near the surface plasmon resonance wavelength of the metallic microparticles, a wavelength at which the metallic microparticles exhibit a large absorption coefficient, or a wavelength near an interband transition for the metallic microparticles is preferred. In this description, a large absorption coefficient refers preferably to an absorption with an intensity of approximately 100 $M^{-1}cm^{-1}$ or greater. For example, in those cases where the microparticles 30 are gold microparticles, the use of a wavelength near the surface plasmon resonance wavelength of approximately 532 nm is preferred. In cases where the microparticles exhibit no strong absorption within the visible spectrum, such as the case where platinum microparticles are used as the microparticles 30, a laser of any wavelength may be used. In those cases where the microparticles 30 do not absorb the laser 24 or the like, or cases where the absorption efficiency for the laser 24 is very low, then as described above, organic dyes or the like that absorb the laser 24 may be incorporated within the microparticles 30.

There are no particular restrictions on the variety of the laser 24 that is used, which may be selected in accordance with the laser wavelength that is desired, and examples of suitable lasers include semiconductor lasers, solid-state lasers, gas lasers, dye lasers, and excimer lasers.

The laser 24 irradiated into the reaction liquid 22 is preferably irradiated through the opening of the cell 14. If the laser is irradiated through the cell 14, then depending on the intensity of the laser 24, the cell 14 itself may undergo sputtering and suffer damage as a result of the irradiation. Furthermore, for the same reasons, the cell 14 is preferably formed from a transparent material. In the example shown in FIG. 1, irradiation of the laser 24 is conducted through the opening 26 in the upper surface of the cell 14.

There are no particular restrictions on the temperature of the reaction liquid 22, provided the temperature is sufficient to ensure efficient decomposition of the target nucleic acid polymer 28, and a typical temperature is within a range from approximately 0° C. to approximately 100° C., and is preferably a room temperature within a range from approximately 10° C. to approximately 30° C.

In a decomposition method according to an embodiment of the present invention, the reaction system need not necessarily be pressurized during irradiation with the laser or the like, and the decomposition usually proceeds at normal pressure. However if required, the reaction system may also be pressurized to a pressure within a range from approximately 0.2 MPa to approximately 100 MPa.

The reaction liquid 22 placed inside the cell 14 is preferably stirred with a dispersion device such as the stirring bar 16 or a stirring blade or the like, thereby stirring and dispersing the addition microparticles 20 within the reaction liquid 22. Furthermore, dispersion can also be conducted using ultrasound as the dispersion device as well as a stirrer. By conducting stirring and dispersion, the laser is able to be irradiated uniformly onto the entire reaction liquid. A stirring device need not be used in those cases where the addition microparticles 20 disperse naturally without the use of a stirring device such as the stirring bar 16.

In this manner, by dispersing or dissolving the addition microparticles 20 in a solvent, and then irradiating a laser 24 or the like onto the addition microparticles 20, energy transfer from the resulting high-energy state microparticles 30 into the immediate surroundings causes decomposition of the target nucleic acid polymer 28 at a specific site. Possible forms for this energy transfer include thermal energy, high-energy component particles of the microparticles 30, or ions or electrons therefrom. Taking the case in which gold microparticles are elevated to a high-energy state by laser irradiation as an example, the energy of the electrons that absorb laser light via surface plasmon resonance is relaxed through vibrational energy within the lattice of the gold microparticles, which causes the solid-state gold microparticles to start to melt. The resulting melt-state gold microparticles then undergo further evaporation, generating atomic gold. It is thought that the high-energy particles such as gold atoms, gold clusters, gold ions, electrons and radicals emitted in this manner from the surface of the high-energy state gold microparticles decompose the target nucleic acid polymer 28 molecules that exist near the surface of the gold microparticles. Furthermore, the emitted electrons are accelerated by the strong electric field of the laser, these electrons collide with and ionize neighboring gold atoms and solvent molecules, and the electrons emitted as a result collide with other molecules, causing an avalanche that results in a shift to a high-energy state such as a plasma state. It is thought that these high-energy particles exist in close proximity to the microparticle surface, within a range of no more than several dozen nm from the microparticle surface, and consequently the site at which the target nucleic acid polymer 28 undergoes decomposition is limited to sites that exist near the surface of the microparticles. In other words, the target nucleic acid polymer site that undergoes decomposition is limited to the sites of several bases that exist near the microparticle surface, meaning a site-specific cleavage is achieved.

Figure 2:
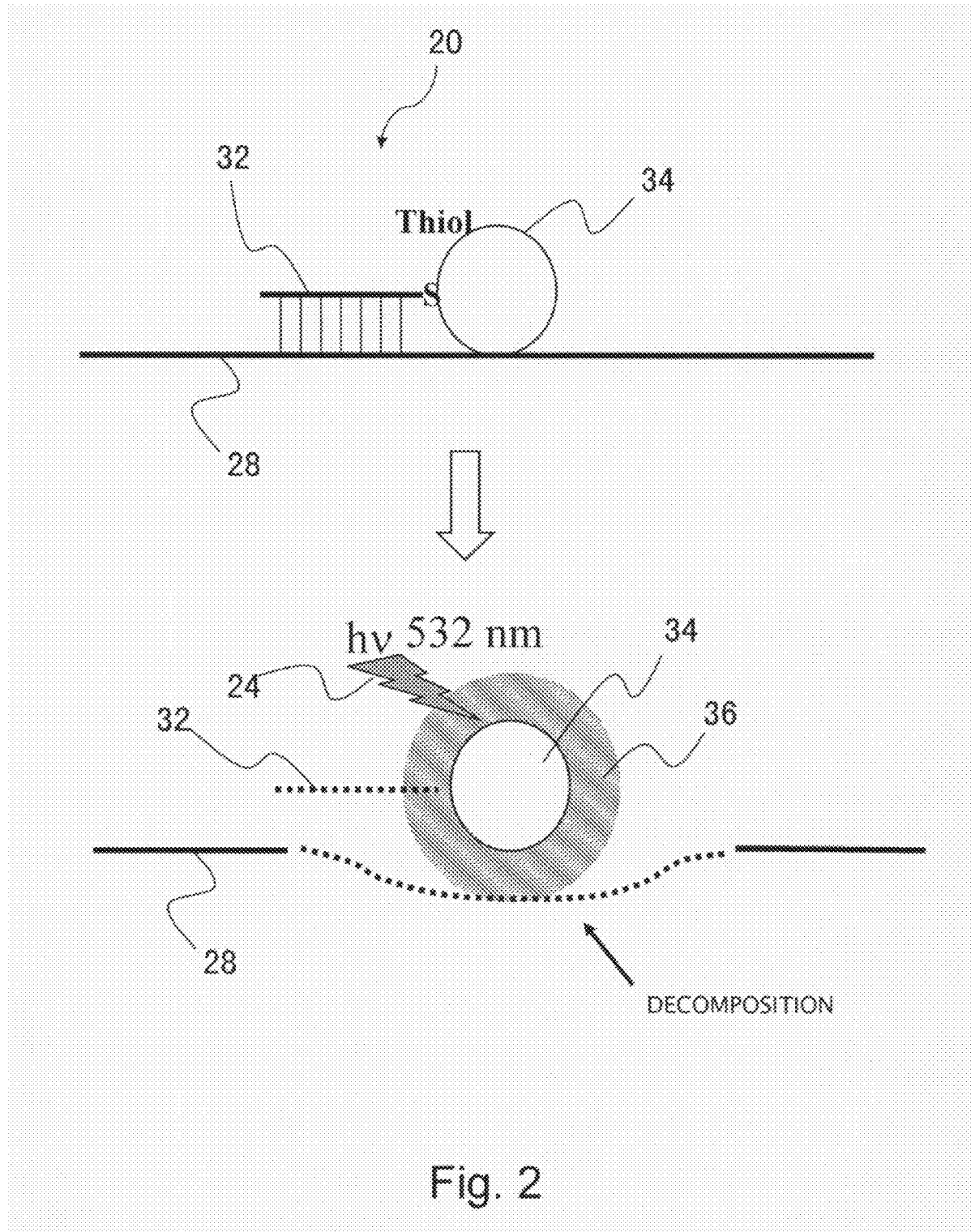
FIG. 2 is a diagram showing a schematic illustration of a nucleic acid polymer decomposition method according to an embodiment of the present invention.

An outline of this decomposition process is shown in FIG. 2. A solution comprising a hybrid (an addition microparticle 20) of a gold microparticle 34 that has been thiol-bonded to a probe nucleic acid polymer 32 with a thiol-labeled terminal (namely, a probe nucleic acid polymer-bonded microparticle) and a target nucleic acid polymer 28 is irradiated with a laser 24, thereby generating a high-energy region 36 surrounding the gold microparticle 34. As a result, the nearby probe nucleic acid polymer 32 and the portion of the target nucleic acid polymer 28 in close proximity to the gold microparticle 34 are decomposed and cleaved.

When a high-intensity laser is irradiated into a solvent such as water, the entire focus region (for example, a region with a volume of at least $(1 \ \mu m)^3$) is usually converted to a plasma state or the like, but in the present embodiment, the entire laser focus region is not converted to a plasma state, but rather only the regions in close proximity to the microparticles that exist within the laser focus region develop a plasma state. Furthermore, because the region that is converted to a plasma state or the like can be controlled by factors such as the average particle size of the microparticles and the intensity of the irradiated laser, by selecting these factors such as the average particle size of the microparticles and the intensity of the irradiated laser in accordance with the desired purpose of the decomposition, the region of the target nucleic acid polymer that undergoes the decomposition reaction can be controlled.

In the present embodiment, the probe nucleic acid polymer 32 and the microparticle 30 are bonded together, and the addition microparticle 20 is then generated by adding the target nucleic acid polymer 28 to the probe nucleic acid polymer 32, and consequently, a specific site of the target nucleic acid polymer 28 exists selectively near the surface of the microparticle 30. Moreover, by irradiating the microparticle 30 with the laser 24 or the like, the specific site of the target nucleic acid polymer 28 can be selectively decomposed. As described above, in the present embodiment, it is thought that the high-energy particles exist almost entirely in close proximity to the surface of the microparticle, and consequently the portion of the target nucleic acid polymer 28 that undergoes decomposition is limited to the portion near the surface of the microparticle, thus enabling a specific site of the target nucleic acid polymer 28 to be selectively decomposed, while other sites of the target nucleic acid polymer 28 that do not exist in close proximity to the surface of the microparticle 30 undergo substantially no decomposition. Furthermore, because the cleavage is effected via a high-energy state surrounding the microparticle, it is unaffected by base modification of the target nucleic acid polymer.

Here, it is thought that the region in which the target nucleic acid polymer undergoes cleavage matches the size of the high-energy region surrounding the microparticle. In this description, the size of the high-energy state region generated surrounding a gold microparticle by laser irradiation is estimated in the manner described below.

In water, an energy density of approximately $10^{10}$ W/cm$^2$ is required to extract the electrons required for plasma formation from the water molecules, but in the example described below, the energy density of the laser irradiation is approximately $10^9$ W/cm$^2$, and is consequently insufficient to generate a laser plasma. On the other hand, at this point it is thought that the gold microparticles have reached a temperature of $10^4$ to $10^5$ K via multiphoton absorption from the laser. Accordingly, it is thought that the work function of the gold is approximately 9.6 eV, and consequently a proportion of gold atoms within a range from approximately $10^{-4}$ to approximately $10^{-3}$ of all the gold atoms that constitute the gold microparticles will emit an electron. Because the density of gold atoms within the gold microparticles is approximately $6.0 \times 10^{22}$ atoms/cm$^3$, the density of emitted electrons from gold nanoparticles reaches at least approximately $10^{19}$/cm$^3$. This quantity is considerably larger than the electron density of approximately $10^{18}$/cm$^3$ required for plasma formation within water.

The generation equation for the free electron density ρ within the solution plasma can be expressed using the equation shown below.

$$\frac{d\rho}{dt} = \eta\rho - g\rho + \left(\frac{d\rho}{dt}\right)m \quad \text{(Equation 1)}$$

The first item on the right side of the equation represents the generation of free electrons by the electron avalanche, wherein η represents the probability of a free electron colliding with a water molecule and withdraw a bonding electron. This process continues throughout the laser pulse, and the free electrons emitted from water molecules in this manner are accelerated by the strong electric field of the laser, thereby causing a reaction that releases more electrons from water molecules. The second item on the right side of the equation represents the change in free electron density caused by recombination, trapping or diffusion of the free electrons. g is a variable that combines these various effects. The last item represents free electrons generated by multiphoton absorption during pulsed irradiation of the laser.

Emission of electrons from the gold microparticles continues throughout the laser irradiation. Accordingly, the size of the plasma may be assumed to be roughly the same as that of the free electron existence region, which contains the free electrons generated from the gold microparticles during the initial stages of the pulsed laser irradiation, and is of a size determined by the effects represented by the aforementioned variable g. As described above, the size of this free electron existence region is determined by effects such as electron recombination, trapping and diffusion. When a free electron absorbs a powerful laser photon, the life span of the free electron is assumed to be longer than the length of the laser pulse. Accordingly, recombination of the electron and hole can be ignored. Furthermore, based on the trapping energy of a local potential well, absorption of a single laser photon is easily sufficient to enable reionization, and consequently this effect can also be ignored.

Based on the above assumptions, it is considered that the size of the free electron existence region is determined by the size of the diffusion region. The size of that region ($d_{upper\ limit}$) is determined by the following equation.

$$d_{upper\ limit} = \sqrt{D\tau_p} \quad \text{(Equation 2)}$$

In this equation, D represents the electron diffusion coefficient and $\tau_p$ represents the pulse width of the irradiated laser. D can be represented by the equation shown below.

$$D = 2\in_{av}/3\ mv \quad \text{(Equation 3)}$$

In this equation, $\in_{av}$ represents the average energy of the electrons and m represents the electron mass. v is the time between water molecule collisions for a free electron. $\in_{av}$ and v can be calculated using the equations shown below.

$$\in_{av} = E_{ion}/2 \quad \text{(Equation 4)}$$

$$v = 1/\tau \quad \text{(Equation 5)}$$

Here, $E_{ion}$ represents the electron binding energy, and τ represents the frequency of water molecule collisions. The work function for gold of 9.6 eV is substituted for the value of $E_{ion}$, and $1.0 \times 10^{-15}$ seconds is used as the value for τ. This leads to a value for D of $5.9 \times 10^{-5}$ m$^2$/sec. As a result, the value of $d_{upper\ limit}$ can be determined as approximately $7.0 \times 10^{-6}$ m. It is thought that the actual size of the plasma is smaller than the value of $d_{upper\ limit}$. This is because no consideration has been made for coulomb interaction between the emitted electrons and positively charged gold microparticles, or for the electron density required for plasma generation. Furthermore, if the assumption is made that all of the gold atoms that constitute the gold microparticles emit an electron, then the resulting electron density is approximately $6.0 \times 10^{22}$ atoms/cm$^3$. The volume that results when this density diffuses uniformly and is reduced to the electron density required for plasma formation is approximately $(10^{-7}$ m$)^3$. It is thought that the portion of the target nucleic acid polymer that exists within this region with a size of approximately $(10^{-7}$ m$)^3$ undergoes decomposition.

Decomposition of the target nucleic acid polymer by the microparticles can be confirmed by measuring the ultraviolet-visible absorption spectrum, infrared absorption spectrum or nuclear magnetic resonance spectrum or the like of the reaction liquid following irradiation with a laser or the like, or by using a method such as high-performance liquid chromatography, gas chromatography or electrophoresis.

In this manner, in a plasma or the like produced by high-energy microparticles that have been generated by a nucleic acid polymer decomposition method according to the present embodiment, space and time can be readily controlled. In other words, by using a nucleic acid polymer decomposition method according to the present embodiment, a plasma or the like can be generated within a much smaller region than that of a discharge plasma, and for example, can be generated within a microregion that is limited to a size within a range from approximately (1 nm)$^3$ to approximately (100 nm)$^3$. This enables the target nucleic acid polymer that exists near the surface of the microparticle to be decomposed at a specific site. Furthermore, in those cases where the microparticles are elevated to a high-energy state using a laser or the like, the plasma can be generated with a nano-order precision within a range from approximately 1 fsec to approximately 100 nsec, meaning control of the time of the target nucleic acid polymer decomposition is far more precise than that achievable using methods that employ restriction enzymes, methods that employ chemically synthesized molecules, or methods that employ a ribozyme.

Furthermore, by encapsulating a probe nucleic acid polymer-bonded microparticle within the interior of a membrane structure such as a cell, hybridizing this probe nucleic acid polymer-bonded microparticle with the DNA or RNA inside the cell, and then elevating the microparticle to a high-energy state using a laser or the like, the DNA or RNA (the target nucleic acid polymer) near the microparticle can be selectively decomposed. In this case, because a plasma state or similar is generated only near the surface of the microparticle, destruction of other substances within other regions can be avoided.

A nucleic acid polymer decomposition method and decomposition apparatus according to the present embodiments can be used for general DNA and RNA analysis applications, medical applications, and applications involving the investigation of the functions of DNA and RNA molecules.

With the development of methods for handling polymers, and particularly biopolymers, the targets of gene manipulation are gradually shifting from lower-order organisms to higher-order organisms, and techniques that enable modifications to manipulate freely on large DNA, RNA, proteins or sugar chains are becoming increasingly important. For example, natural restriction enzymes are useful in the gene manipulation of plasmid DNA, but if the giant DNA of higher-order organisms are treated in a similar manner with such restriction enzymes, then cleavage occurs at a vast number of sites, making accurate gene manipulation impossible. However if, as in the present embodiments, probe nucleic acid polymer-bonded microparticles formed by bonding together microparticles, particularly metallic microparticles, and a probe nucleic acid polymer are used to effect hybridization at a specific site of a target nucleic acid polymer, and these microparticles are then elevated to a high-energy state, then a site-specific cleavage of the target nucleic acid polymer can be achieved. The greatest advantages of this method are that (1) cleavage can be conducted with the desired site specificity, even for giant DNA, and (2) preparation of the probe nucleic acid polymer is far simpler than in other methods. By using this method, expression of the function of a target RNA can be eliminated, and the expression of disease or disorder-causing genes can also be prevented in vivo.

In this manner, a nucleic acid polymer decomposition method and decomposition apparatus according to the present embodiments enable the cleavage of solely specific sites of nucleic acid polymers such as DNA and RNA to be conducted with good reproducibility, and are able to dramatically improve the efficiency of genetic analysis.

EXAMPLES

As follows is a more detailed description of the present invention based on a series of examples, although the present invention is in no way limited to the examples presented below.

Example 1

Preparation of Gold Microparticles

Gold microparticles are prepared by a method involving the reduction of HAuCl$_4$ by citric acid. 10 mL of a 1 mM aqueous solution of HAuCl$_4$ is heated with constant stirring to establish the appropriate reduction conditions. To this solution is quickly added 38.8 mM of trisodium citrate. Once the color of the solution changes from yellow to a deep red, the solution is stirred for a further 15 minutes. The solution is then cooled to room temperature (25° C.), and filtered through a filter with a pore size of 0.45 µm. The average particle size of the gold microparticles synthesized in this manner is adjusted to 13 nm by adjusting the concentrations of the HAuCl$_4$ and the citric acid.

<Preparation of Probe Nucleic Acid Polymer-Bonded Microparticles by Bonding Gold Microparticles and Probe DNA>

A probe DNA with a thiolated terminal (50 mer) is mixed, at a concentration of 5 µM, with the aqueous solution containing the gold microparticles with an average particle size of 13 nm, and the resulting solution is left to stand for 16 hours. The solution is then adjusted to a buffered solution (pH=7.0) using 0.1 M of NaCl and 10 mM of phosphoric acid, and the solution is left to stand for a further 40 hours. A combined operation involving centrifuging and re-dispersion is then repeated 3 times for removal of any excess material.

Figure 3:
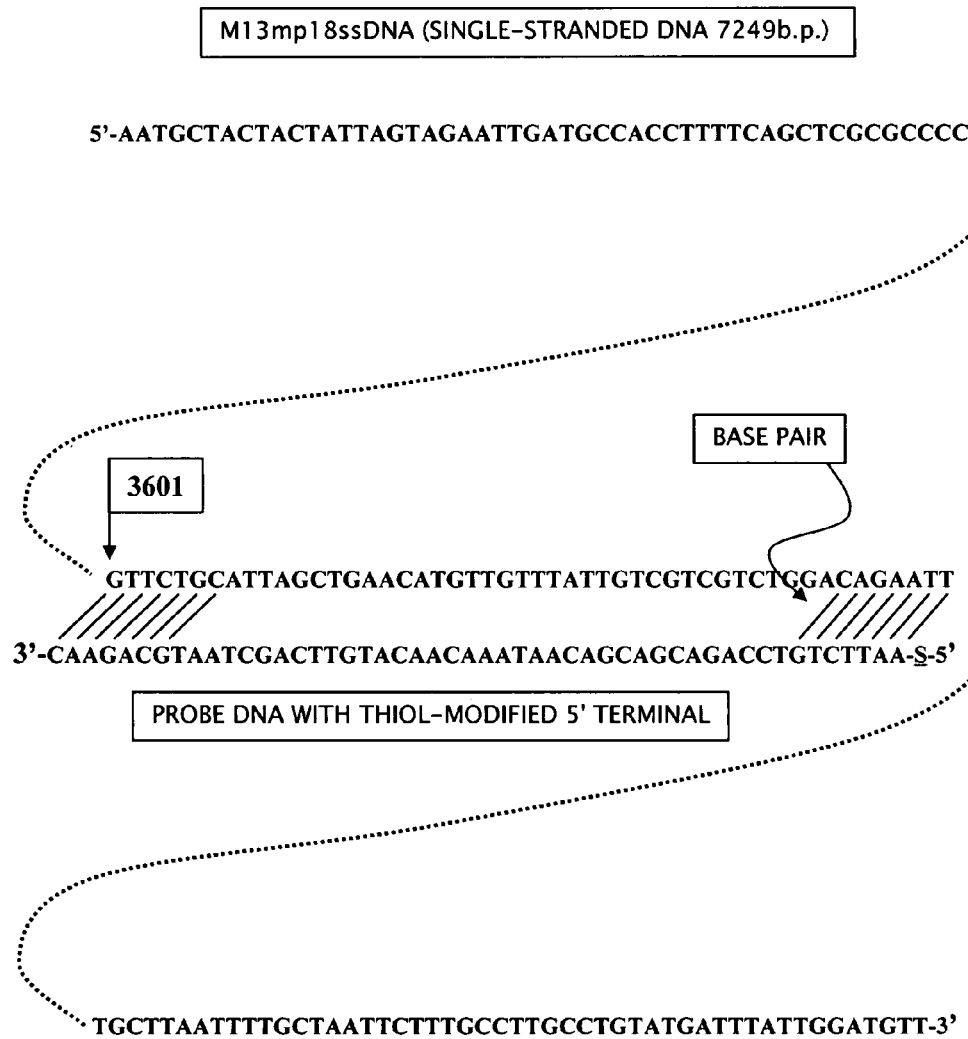
FIG. 3 is a diagram showing the sequence of a probe DNA (SEQ ID NO: 2) and target DNA (Nucleotides 1-50, 3601-3650 and 7200-7249 of SEQ ID NO: 1, respectively, in order of appearance) used in an example 1 of the present invention.

FIG. 3 shows the base sequence of the probe nucleic acid and a target nucleic acid M13mp18ssDNA 7249 b.p. used in this example 1. The probe nucleic acid is designed to form a base pair beginning from base number 3601 of the target nucleic acid. Furthermore, the 5' terminal of the probe nucleic acid is thiol-labeled, and bonds to a gold microparticle.

<Confirmation of Hybridization of Probe Nucleic Acid Polymer-Bonded Microparticles Generated by Bonding Gold Microparticles and Probe DNA, and Target DNA>

The target DNA M13mp18ssDNA (single-stranded DNA 7249 b.p.) and the above probe nucleic acid polymer-bonded microparticles are mixed together, and held at a temperature of 60° C. for 5 minutes. The mixture is then left to stand for a further 3 hours at room temperature (25° C.). Analysis by agarose gel electrophoresis reveals that this is insufficient to achieve hybridization. Assuming that the standing time is insufficient, the mixture is left to stand for 48 hours at 50° C. Analysis by agarose gel electrophoresis confirms hybridization. Photographs of the gel are shown in FIG. 4 and FIG. 5.

Figure 4:
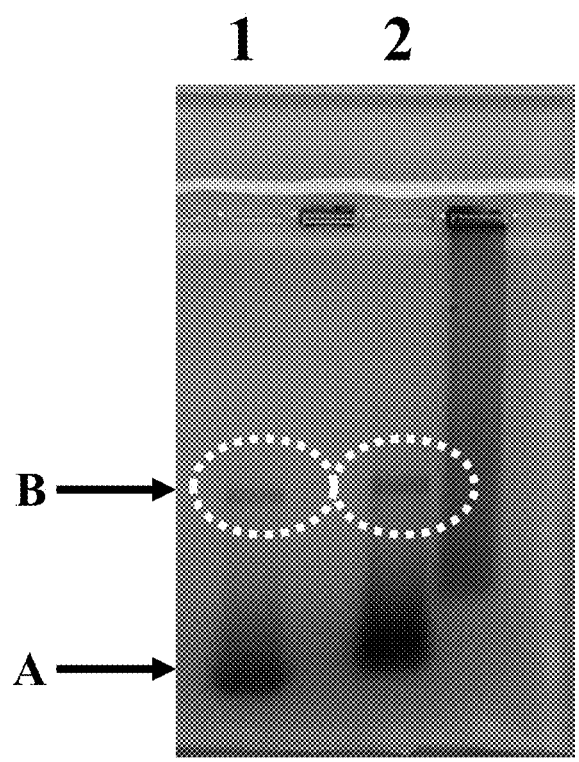
FIG. 4 is a photograph showing agarose gel of electrophoresis of a reaction liquid following hybridization in the example 1 of the present invention.
Figure 5:
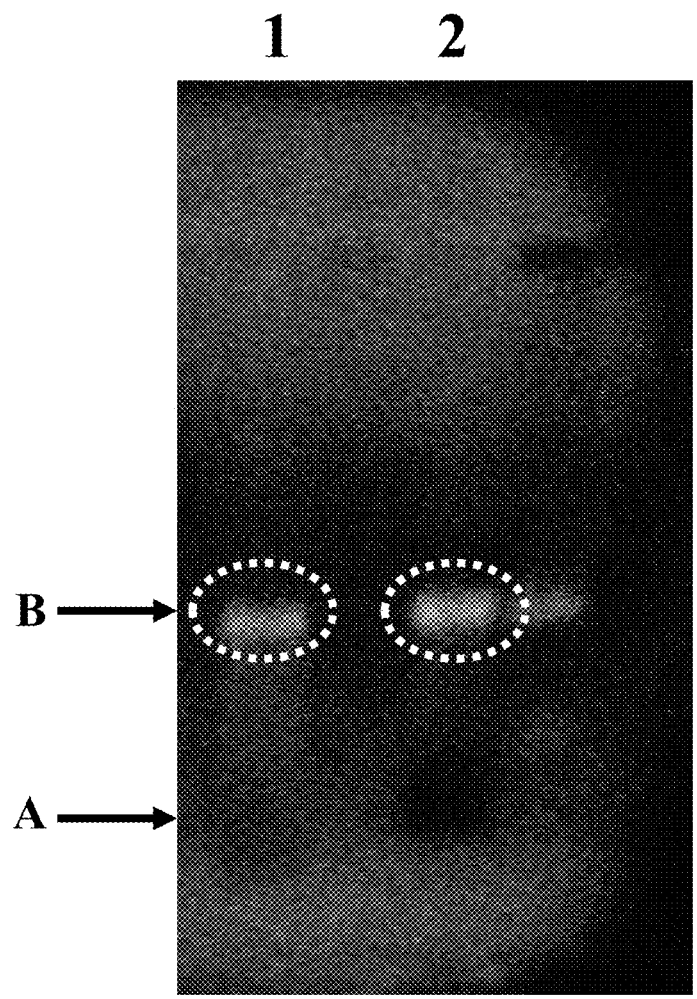
FIG. 5 is a photograph showing agarose gel of electrophoresis upon UV irradiation of a reaction liquid following hybridization in the example 1 of the present invention.

As is evident from FIG. 4, the gold microparticles bonded to the probe DNA that is hybridized with the target DNA cause electrophoresis within the agarose while still in a hybridized state. This is observed as a deep red band at a position indicated by an arrow B in lanes 1 and 2 within the agarose (indicated by a dotted line in the figure). The arrow A indicates the electrophoresis front. At the front indicated by the arrow A, probe DNA that has not hybridized with the target DNA is observed via a deep red band of the gold microparticles bonded thereto. Furthermore, if UV is irradiated onto this gel, then as is evident from FIG. 5, a fluorescent band of a dye that is intercalated with the target DNA is observed at the same position as the gold microparticles band shown in FIG. 4, that is, at a position indicated by the arrow B in lanes 1 and 2 (and indicated by a dotted line in the figure). The arrow A indicates the electrophoresis front. This indicates that the probe DNA with gold microparticle bonded thereto is hybridized with the target DNA. Here, the solution is adjusted to a pH of 7.0 using a phosphoric acid buffer, and 0.1 M of NaCl is then added.

<Cleavage of Target DNA by Laser Irradiation>

50 µL of the above solution containing the hybrid (addition microparticles) of the probe DNA with gold microparticles bonded thereto and the target DNA is placed in a cell with a bottom surface area of 0.5 cm×0.5 cm, and is then irradiated for 5 minutes with a laser of wavelength 532 nm having a single pulse intensity of 4 mJ. Using a lens, the laser light is focused within a region with a volume of approximately $(0.1 \text{ mm})^3$ inside the solution. During this irradiation, the solution is stirred by placing a stirring bar of length 2 mm and width 1 mm in the bottom of the cell. Because the wavelength of 532 nm coincides with the surface plasmon resonance of the gold microparticles, the gold microparticles are able to be efficiently elevated to a high-energy state. Confirmation of the cleavage of the target DNA is conducted by agarose gel electrophoresis.

Figure 6:
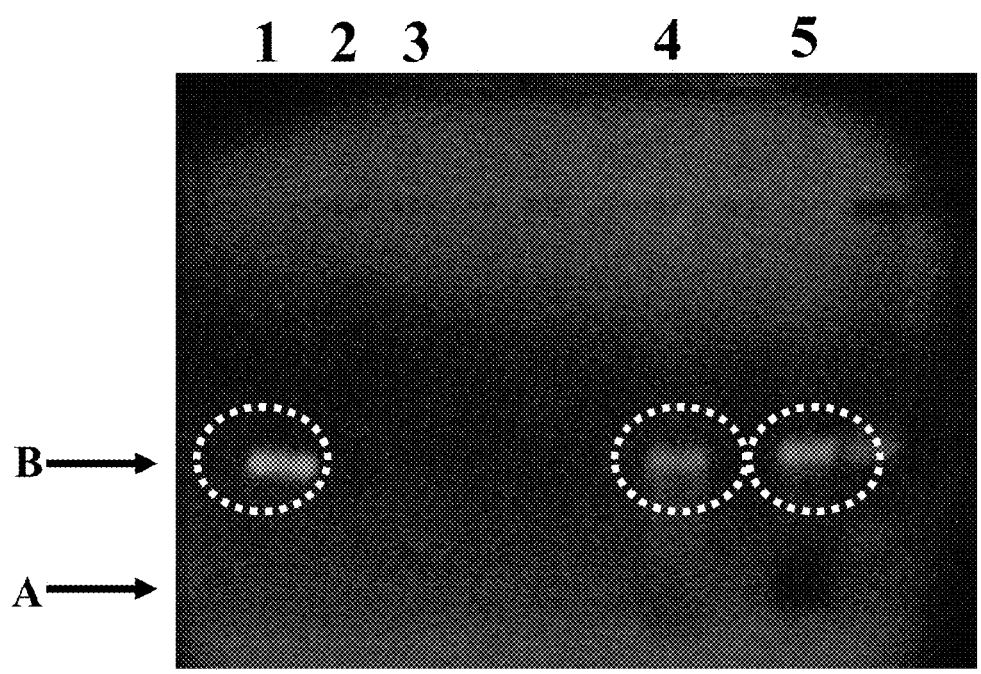
FIG. 6 is a photograph showing agarose gel of electrophoresis before and after laser irradiation of a solution of the example 1 of the present invention that comprises a hybrid of a target DNA and a probe DNA with a gold microparticle bonded thereto.

FIG. 6 shows the solution agarose gel electrophoresis before and after laser irradiation (4 mJ/pulse) of the solution containing the hybrid of the target DNA (M13ssDNA) and the probe DNA with gold microparticles bonded thereto. The arrow A indicates the electrophoresis front, and the arrow B indicates the position of the M13ssDNA band. The result of subjecting the solution of lane 4 to laser irradiation is shown in lane 2, and the result of subjecting the solution of lane 5 to laser irradiation is shown in lane 3. The fact that the M13ssDNA band visible in lanes 4 and 5 (shown within the dotted line in the figure) is not visible in the lane 2 and 3 shows that the M13ssDNA band has been eliminated following laser irradiation, indicating that the M13ssDNA has undergone cleavage. It is believed that the reason for this observation is that the target DNA has been decomposed into DNA fragments with molecular weights that are too small to be confirmed by agarose gel electrophoresis. Lane 1 shows the electrophoresis for only M13ssDNA, which is used for confirming the position of the M13ssDNA band (indicated by the dotted line in the figure).

Example 2

Hybridization of Probe Nucleic Acid Polymer-Bonded Microparticles Generated by Bonding Gold Microparticles and Probe DNA, and Target DNA, and Confirmation Thereof A target DNA M13mp18ssDNA (a single-stranded DNA 7249 b.p.) (concentration: $1.8 \times 10^{-8}$ M) is mixed with gold microparticles bonded to probe DNA comprising either DNA-1 or DNA-2 respectively shown in FIG. 7 (concentration: $5.4 \times 10^{-8}$ M), and each mixture is held at a temperature of 30° C. The solution is then adjusted to a pH of 7.0 using a phosphoric acid buffer (0.01 M), and sufficient NaCl is then added to produce a NaCl concentration of 0.1 M.

Figure 7:
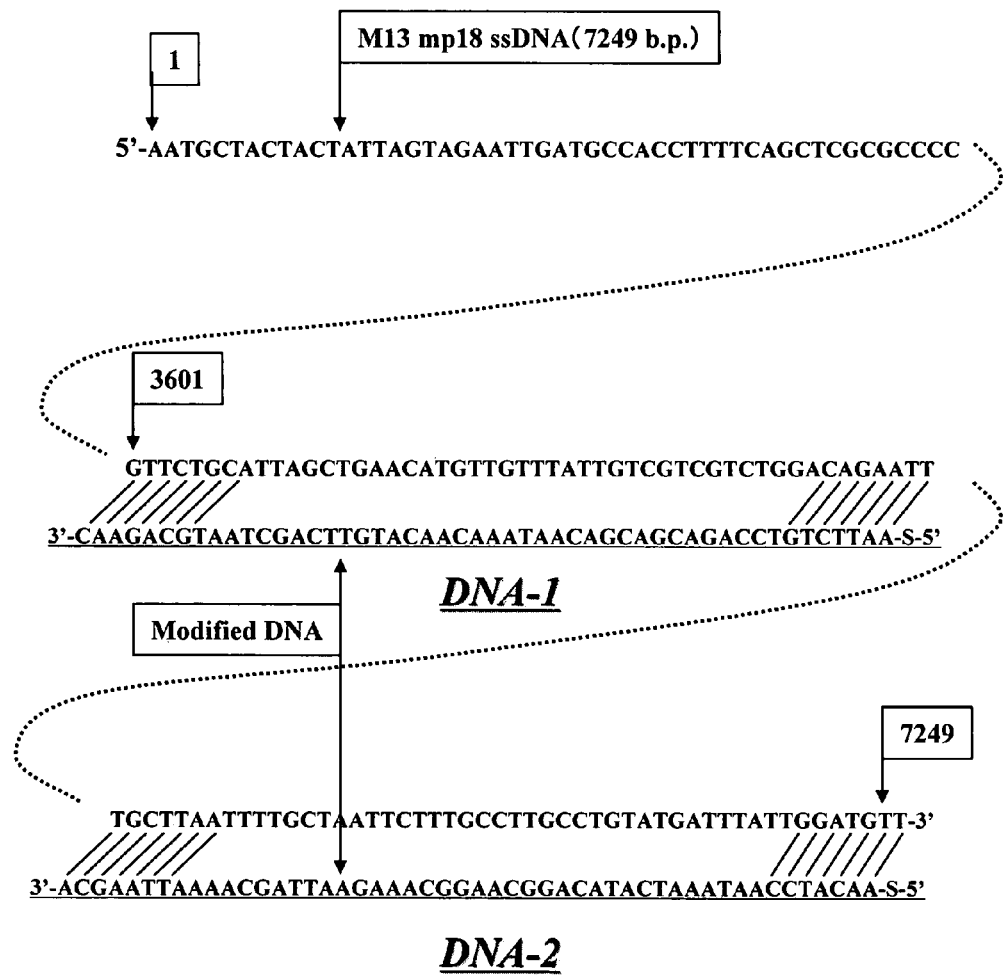
FIG. 7 is a diagram showing the sequence of a probe DNA (SEQ ID NOS 2-3, respectively, in order of appearance) and target DNA (Nucleotides 1-50, 3601-3650 and 7200-7249 of SEQ ID NO: 1, respectively, in order of appearance) used in an example 2 of the present invention.

FIG. 7 shows the base sequence of the probe DNA and target DNA M13mp18ssDNA 7249 b.p. used in this example 2. The probe DNA-1 (50 mer) is designed to form a base pair beginning from base number 3601 of the target DNA, whereas the probe DNA-2 (50 mer) is designed to form a base pair beginning from base number 7199 of the target DNA. Furthermore, the 5' terminal of each of the probe nucleic acids is thiol-labeled and bonded to a gold microparticle.

<Cleavage of Target DNA by Laser Irradiation>

Figure 8:
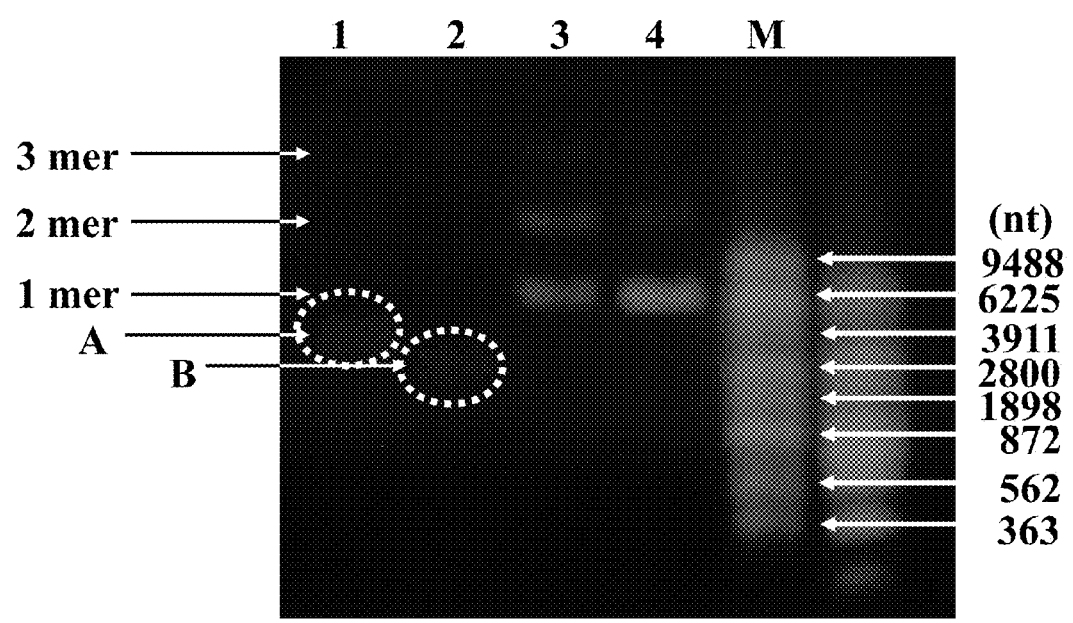
FIG. 8 is a photograph showing agarose gel of electrophoresis of a reaction liquid before and after laser irradiation in the example 2 of the present invention.

Each of the prepared solutions containing the hybrid (addition microparticles) of the probe DNA with gold microparticles bonded thereto and the target DNA is irradiated for 5 minutes with a laser of wavelength 532 nm having a single pulse intensity of 2 mJ (a weaker laser intensity than that used in the example 1). Confirmation of the cleavage of the target DNA is conducted by agarose gel electrophoresis. The result is shown in FIG. 8. Lane 1 and lane 2 show the results following laser irradiation for the cases where DNA-2 and DNA-1 respectively are used as the probe DNA, lane 3 and lane 4 show the results prior to laser irradiation for the cases where DNA-2 and DNA-1 respectively are used as the probe DNA, M shows an RNA marker, and the numbers down the right side of the figure represent base numbers. The labels 1, 2 and 3 mer shown down the left side of the figure show the number of target nucleic acids hybridized with a single gold microparticle, and the labels A and B indicate the positions of detected bands derived from cleavage products from the target DNA (indicated by dotted lines in the figure) Agarose gel electrophoresis confirms that the target DNA is cleaved into DNA fragments of differing length, depending on the position of the target site.

What is claimed is:

1. A method for decomposing a target nucleic acid polymer, comprising:
bonding a probe nucleic acid polymer and a microparticle of gold to form a probe nucleic acid polymer-bonded microparticle,
hybridizing a target nucleic acid polymer to the probe nucleic acid polymer contained within the probe nucleic acid polymer-bonded microparticle to form an addition microparticle, wherein the target nucleic acid polymer is a single-stranded nucleic acid polymer; and
irradiating the gold microparticle with a laser wherein the laser irradiation conditions are controlled for energizing the microparticle contained within the addition microparticle into a high-energy state and decomposing only specific sites of the target nucleic acid polymer;
wherein the specific sites of the target nucleic acid polymer to be decomposed are located at a region extending no more than approximately 100 nm from a surface of the microparticle.

2. The method according to claim 1, wherein a region that is generated in the high-energy state is a microregion.

3. The method according to claim 2, wherein
the microregion extends no more than approximately 100 nm externally or internally from the surface of the microparticle.

4. The method according to claim 1, wherein the microparticle exhibits surface plasmon resonance in a visible region.

5. The method according to claim 1, wherein an average particle size of the microparticle is within a range from approximately 1 nm to approximately 100 nm.

6. The method according to claim 1, wherein the target nucleic acid polymer is at least one of DNA and RNA.

7. The method according to claim 1, wherein the probe nucleic acid polymer is at least one of DNA and RNA and PNA of approximately 10 mer to approximately 50 mer.

8. A method for decomposing a target nucleic acid polymer, comprising:
bonding a probe nucleic acid polymer and a microparticle of gold to form a probe nucleic acid polymer-bonded microparticle;
hybridizing a target nucleic acid polymer to the probe nucleic acid polymer contained within the probe nucleic acid polymer-bonded microparticle to form an addition microparticle, wherein the target nucleic acid polymer is a single-stranded nucleic acid polymer;
energizing by irradiation the microparticle contained within the addition microparticle into a high-energy state by means of a laser, wherein the laser is focused into a region with a volume within a range from approximately 1 $\mu m^3$ to approximately 1 $mm^3$, and the laser is a pulse laser having a laser intensity in a range from approximately 100 µJ/pulse to approximately 100 mJ/pulse; and
then emitting high-energy particles, including gold atoms, gold clusters, gold ions, electrons and radicals from the high-energy state microparticle to decompose specific sites of the target nucleic acid polymer only in a region no more than approximately 100 nm from a surface of the microparticle without converting an entire irradiating region to a plasma state.

* * * * *